US010577250B2

(12) United States Patent
Maio et al.

(10) Patent No.: US 10,577,250 B2
(45) Date of Patent: Mar. 3, 2020

(54) PROCESS FOR PRODUCING OF INORGANIC PARTICULATE MATERIAL

(71) Applicant: Merck Patent GmbH, Darmstadt (DE)

(72) Inventors: Mario Maio, Milan (IT); Eugenia Breininger, Kandel (DE); Karin Cabrera Perez, Dreieich (DE); Ulrich Lang, Heppenheim (DE); Benjamin Peters, Muenster (DE); Thomas Puchert, Soest (DE); Christoph Saal, Otzberg (DE); Michael Schulz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 116 days.

(21) Appl. No.: 15/346,377

(22) Filed: Nov. 8, 2016

(65) Prior Publication Data
US 2017/0049892 A1 Feb. 23, 2017

Related U.S. Application Data

(62) Division of application No. 14/117,041, filed as application No. PCT/EP2012/001769 on Apr. 25, 2012, now Pat. No. 9,517,268.

(30) Foreign Application Priority Data

May 13, 2011 (EP) .................... 11003961

(51) Int. Cl.
A61K 9/16 (2006.01)
A61K 47/02 (2006.01)
(Continued)

(52) U.S. Cl.
CPC ............ C01B 33/18 (2013.01); A61K 9/1611 (2013.01); A61K 31/496 (2013.01); A61K 47/02 (2013.01); C01B 33/155 (2013.01); C01B 33/157 (2013.01); C01P 2004/30 (2013.01); C01P 2006/17 (2013.01)

(58) Field of Classification Search
None
See application file for complete search history.

(56) References Cited

U.S. PATENT DOCUMENTS 6,107,351 A    8/2000  Burns et al.
6,207,098 B1   3/2001  Nakanishi et al.
(Continued)

FOREIGN PATENT DOCUMENTS

CN    1541186 A    10/2004
CN    1777411 A    5/2006
(Continued)

OTHER PUBLICATIONS

Official Action related to the corresponding Chinese Application No. 201280023311.9, dated Jan. 14, 2015.
English translation of CN101829331 published Sep. 15, 2010 to UNIV Shenyang Pharmaceutical.
Chinese Office Action dated Jul. 14, 2016, issued in corresponding Chinese Application No. 201280023311.9, 9 pages.
(Continued)

Primary Examiner — Bethany P Barham
Assistant Examiner — Barbara S Frazier
(74) Attorney, Agent, or Firm — Millen White Zelano and Branigan, PC; Csaba Henter

(57) ABSTRACT

The present invention is directed to a process for producing inorganic particulate material, the material obtainable by such process, a modified release delivery system comprising the material and the use of the material for the administration of a bioactive agent.

20 Claims, 1 Drawing Sheet

Dissolution rate of itraconazole

(51) Int. Cl.
　　　*C01B 33/155*　　(2006.01)
　　　*C01B 33/157*　　(2006.01)
　　　*C01B 33/18*　　(2006.01)
　　　*A61K 31/496*　　(2006.01)

(56) References Cited

U.S. PATENT DOCUMENTS

| | | |
|---|---|---|
| 6,562,744 B1 | 5/2003 | Nakanishi et al. |
| 8,992,974 B2 | 3/2015 | McCarty |
| 2004/0170694 A1 | 9/2004 | Colic |
| 2005/0032965 A1 | 2/2005 | Valero |
| 2007/0003492 A1 | 1/2007 | Kitahata et al. |
| 2007/0071806 A1 | 3/2007 | McCarty |
| 2007/0224133 A1 | 9/2007 | McGill |
| 2009/0291144 A1 | 11/2009 | Colic |
| 2010/0221541 A1 | 9/2010 | Valero et al. |
| 2014/0336274 A1 | 11/2014 | Maio |

FOREIGN PATENT DOCUMENTS

| | | |
|---|---|---|
| CN | 101113247 A | 1/2008 |
| CN | 101250313 A | 8/2008 |
| CN | 101343065 A | 1/2009 |
| CN | 101348713 A | 1/2009 |
| CN | 101412517 A | 4/2009 |
| CN | 101559952 A | 10/2009 |
| CN | 101829331 A | 9/2010 |
| EP | 0 952 965 B1 | 10/2001 |
| EP | 1298097 A1 | 4/2003 |
| EP | 1702886 A1 | 9/2006 |
| GB | 1070216 A | 6/1967 |
| JP | 10182260 A | 7/1998 |
| JP | 10182261 A | 7/1998 |
| JP | 11292528 A | 10/1999 |
| JP | 2007523817 A | 8/2007 |
| JP | 2009013142 A | 1/2009 |
| JP | 2014522363 A | 9/2014 |
| WO | 03/016215 A1 | 2/2003 |
| WO | 2004075877 A1 | 9/2004 |
| WO | 2005026048 A1 | 3/2005 |

OTHER PUBLICATIONS

Machine Translation of Description, Claims and Abstract of CN 101113247 (A)—Jan. 30, 2008.
Machine Translation of Description, Claims and Abstract of CN 101250313 (A)—Aug. 27, 2008.
Machine Translation of Description, Claims and Abstract of CN 101343065 (A)—Jan. 14, 2009.
Machine Translation of Description, Claims and Abstract of CN 101348713 (A)—Jan. 21, 2009.
Machine Translation of Description, Claims and Abstract of CN 101412517 (A)—Apr. 22, 2009.
Machine Translation of Description, Claims and Abstract of CN 101559952 (A)—Oct. 21, 2009.
Notification of the Second Official Action relating to Chinese Patent Application No. 201280023311.9—dated Sep. 6, 2015.
Machine Translation of Description, Claims and Abstract of JPH 10182260 (A)—Jul. 7, 1998.
Machine Translation of Description, Claims and Abstract of JPH 10182261 (A)—Jul. 7, 1998.
Machine Translation of Description, Claims and Abstract of JPH 11292528 (A)—Oct. 26, 1999.
Machine Translation of Description, Claims and Abstract of JP 2007523817 (A)—Aug. 23, 2007.
Machine Translation of Description, Claims and Abstract of JP 2009013142 (A)—Jan. 22, 2009.
Machine Translation of Description, Claims and Abstract of WO 2005026048 A1—Mar. 24, 2005.
Skudas, Romas et al., "Impact of pore structural parameters on col. performance and resolution of reversed-phase monolithic silica columns for peptides and proteins", Journal of Chromatography A, 1144 (2007)—pp. 72-84.
Unger, Klaus K., et al., "Particle packed columns and monolithic columns in high-performance liquid chromatography-comparison and critical appraisal", Journal of Chromatography A, 1184 (2008)—pp. 393-415.
Ali, Imran, et al., "Monolithic Silica Stationary Phases in Liquid Chromatography", Journal of Chromatographic Science, vol. 47, Jul. 2009, pp. 432-442.
Unger K.K., Porous Silica; Journal of Chromatography. vol. 16, pp. 147-151 (1979).

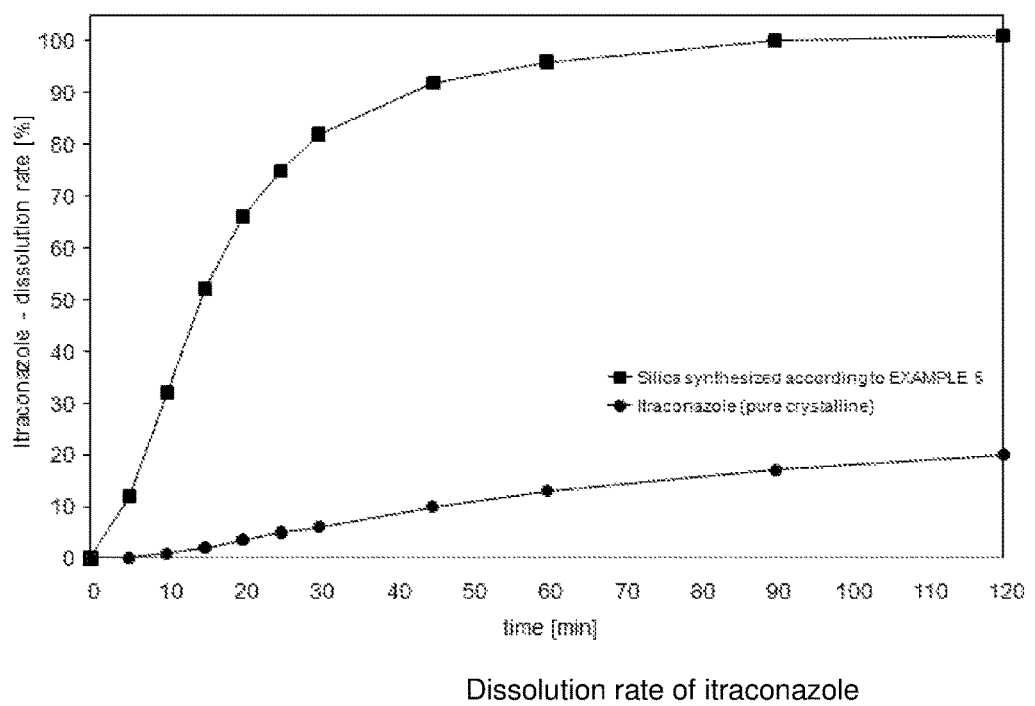
Dissolution rate of itraconazole

PROCESS FOR PRODUCING OF INORGANIC PARTICULATE MATERIAL

The present invention is directed to a process for producing inorganic particulate material, the material obtainable by such process, a modified release delivery system comprising the material and the use of the material for the administration of a bioactive agent.

Inorganic materials are receiving a great interest in the field of biomedical science in the last few years. Two main routes have been traditionally used for drug intake: oral administration and injection. Traditional therapies are characterized by an increase of drug concentration in plasma when the intake takes place, followed by a decrease, leading to a sinusoidal behavior of the drug concentration in plasma vs. time.

Inorganic materials, especially bioceramics, have some porosity that can be used for drug delivery including chemically synthesized substances such as, for example, ibuprofen or nimodipine, but also biologically derived substances such as, for example, releasing growth factors or proteins. Especially silica-based ordered mesoporous materials are possible candidates as reservoir bioceramics where drugs can be confined.

These materials are characterized by large specific surface areas, ordered pore systems, and narrow pore size distributions. In addition, these mesoporous materials have been reported to be excellent candidates to be used in tissue engineering nanotechnology, because they show the capability to perform as controlled delivery systems of a wide range of drugs and to promote bone tissue regeneration.

Depending of their pore size inorganic materials can be classified as microporous, mesoporous or macroporous. Within the meaning of the present application microporous materials are understood to have a pore size <2 nm, mesoporous materials are understood to have a pore size from 2 to 100 nm and macroporous materials are understood to have a pore size >100 nm.

In recent years ordered porous materials have been increasingly studied for the use as drug delivery systems. From such materials mesoporous silica has been of specific interest.

One main approach for using mesoporous silica for the formulation of drug delivery systems is to increase the dissolution rate of poorly water-soluble or water-insoluble active pharmaceutical ingredients. Poorly water-soluble or insoluble active pharmaceutical ingredients usually have a very low bioavailability due to their poor solubility in digestive fluids causing incomplete absorption. The rationale of using mesoporous silica for use in drug delivery systems is to increase the dissolution rate of poorly water-soluble or water-insoluble active pharmaceutical ingredients and thereby to improve their bioavailability.

Ordered mesoporous materials, which have been extensively studied, are e.g. MCM-41 (Mobil Composition of Matter number forty one) and SBA-15 (Santa Barbara Amorphous number fifteen). SBA-15 was first described by Zhao et al. and is the result of a templating procedure based on a hexagonal arrangement of amphiphilic block copolymers (D. Y. Zhao et al.: Triblock copolymer syntheses of mesoporous silica with periodic 50 to 300 angstrom pores, Science 279 (1998) 548-552). MCM-41 is obtained by the template action of long chain alkylammonium surfactant molecules (J. S. Beck et al.: A new family of mesoporous molecular sieves prepared with liquid-crystal templates, J. Am. Chem. Soc. 114 (1992) 10834-10843). Typically, the pore diameter varies between 2 and 6 nm for MCM-41 and between 4 and 13 nm for SBA-15. In addition to the well-defined mesopore system, SBA-15 has a complementary pore system comprised of micropores (pore size<2 nm). These micropores are located in the walls between adjacent mesopores and do not bridge the wall; they constitute dead end pores (J. S. Beck et al.: A new family of mesoporous-molecular sieves prepared with liquid-crystal templates, J. Am. Chem. Soc. 114 (1992) 10834-10843).

Vallet-Regi et al. were one of the first to explore the drug release properties of these materials in an attempt to prolong the release of ibuprofen using MCM-41 as a carrier (M. Vallet-Regi et al.: A new property of MCM-41: drug delivery system, Chem. Mater. 13 (2001) 308-311). The release kinetics of drugs from mesoporous silica carriers is dependent on several material characteristics including pore size (P. Horcajada et al.: Influence of pore size of MCM-41 matrices on drug delivery rate, Microporous Mesoporous Mater. 68 (2004) 105-109), pore connectivity (J. Andersson et al.: Influences of material characteristics on ibuprofen drug loading and release profiles from ordered micro- and mesoporous silica matrices, Chem. Mater. 16 (2004) 4160-4167) and the chemical composition of the silica surface (B. Munoz et al.: MCM-41 organic modification as drug delivery rate regulator, Chem. Mater. 15 (2003) 500-503).

WO 2006/026840 A2 discloses a controlled release delivery system wherein amorphous mesoporous non-fibrous silica is used as matrix carrier for the release of bioactive compounds and wherein such matrix carrier further comprises micropores having a mean size in the range of 0.4 to 2.0 nm.

WO 2005/000740 A2 discloses a crystalline mesoporous silica material comprising a framework of zeolite type micropores (designated as nanometer size building units), which does not give rise in Bragg type diffraction in x-ray diffraction, and its use for drug delivery.

Z. G. Shi et al. describe mesoporous silica particles for drug delivery, which beside the mesopores further contain macropores (Z. G. Shi et al.: Drug delivery devices based on macroporous silica spheres, Micropor. Mesopor. Mater. 126 (2011) 826-831). Due to its penetrable macropores the mesopores of such material can be sufficiently and efficiently loaded with drug.

The silica particles described by said publication from Z. G. Shi et al. are produced by using sol-gel technique in combination with an emulsion method and phase separation as described by Z. G. Shi et al. in 2008 (Z. G. Shi et al.: Synthesis and characterization of hierarchically porous silica microspheres with penetrable macropores and tunable mesopores, Micropor. Mesopor. Mater. 116 (2008) 701). In brief a solution containing tetraethoxyorthosilicate (TEOS), polyethylene oxide and hydrochloric acid are mixed and stirred and the ethanol resulting from the hydrolization of TEOS is removed by vacuum pumping for 4 h. Then the resulting solution is dispersed into paraffin oil under vigorous stirring. 20 hours later the resulting product was repeatedly washed with ethanol and water and subsequently calcined for 2 h at 600° C. The obtained calcined silica was size classified by using liquid elutriation involving the steps dispersion of the silica particles into water by ultrasonic treatment for 5 min., subsiding the particles in the dispersion by keeping it static for 2 hours, and discarding the upper water solution containing the small particles. Such size-classification was repeated for five times and the particles were collected.

As set forth above the combination of mesoporosity with macroporosity in the silica particles is advantageous for drug loading and release. However, as described above, the method for producing such material is complicated and requires a multitude of different steps such as vacuum pumping, particle formation in paraffin oil, repeated washing and size classification steps of the particles. Therefore, there is the need for a more simplified method of production of mesoporous silica particles, which also comprises macropores.

It has been found by the present invention that an inorganic particulate material mainly composed of silicon oxide, wherein the particulate material comprises mesopores and macropores, can be easily provided by a process comprising the following steps:
(a) dissolving a water-soluble polymer or another pore forming agent and a precursor for a matrix dissolving agent in a medium that promotes the hydrolysis of the metalorganic compound (see step b);
(b) mixing a metalorganic compound or a mixture of metalorganic which contains hydrolyzable ligands to promote hydrolysis reaction;
(c) solidifying the mixture through a sol-gel transition, whereby a gel is prepared which has three dimensional interconnected phase domains with one rich in solvent and the other rich in inorganic component in which surface pores are contained;
(d) disintegrating the gel into particles;
(e) setting the matrix dissolving agent free from its precursor, whereby the matrix dissolving agent modifies the structure of said inorganic component; (f) removing the solvent by evaporation drying and/or heat-treatment;
(g) calcining the particles to form the porous material.

Accordingly the invention is directed to a process for producing inorganic particulate material mainly composed of silicon oxide, wherein the particulate material comprises mesopores and macropores and the process includes the steps of:
(a) dissolving a water-soluble polymer or another pore forming agent and a precursor for a matrix dissolving agent in a medium that promotes the hydrolysis of the metalorganic compound (see step b);
(b) mixing a metalorganic compound or a mixture of metalorganic compounds which contains hydrolyzable ligands to promote hydrolysis reaction;
(c) solidifying the mixture through a sol-gel transition, whereby a gel is prepared which has three dimensional interconnected phase domains one rich in solvent the other rich in inorganic component in which surface pores are contained;
(d) disintegrating the gel into particles;
(e) setting the matrix dissolving agent free from its precursor, whereby the matrix dissolving agent modifies the structure of said inorganic component;
(f) removing the solvent by evaporation drying and/or heat-treatment.

In a preferred embodiment of the invention the process as set forth above comprising the steps (a) to (f) further comprises the step (g) calcining the particles.
The process of the invention leads to particulate material having a mean diameter from about 1 μm to about 2000 μm, preferably from about 1 μm to 1000 μm and more preferably from about 1 μm to 500 μm.

Advantageously all steps of the process can be performed in the same reaction vessel (one point reaction), whereas the process described in the prior art involves an emulsification step, which requires distribution of the solution containing the water-soluble polymer (polyethylene oxide) and the metal organic compound (TEOS) in a different vessel containing paraffin oil. Preferably the vessel used for the process is a closable one, which allows the formation saturated vapor pressure, so that the liberation of the matrix dissolving agent from its precursor can be performed in an easy and time efficient manner as described later on. Surprisingly, the process of the invention leads to particulate material having a uniform particle size distribution, which can be adjusted to the requirements by controlling the process conditions. Advantageously time-consuming and expensive size classification steps as well as the loss of material caused by such classification steps can be avoided.

The process of the invention is based on the classical sol-gel method as known in the art, which in principle is a gel formation of metalorganic compound by polymerization under suitable conditions. When a metalorganic compound having hydrolyzable ligands is hydrolyzed by mixing with an acidic aqueous solution of water-soluble polymer or some other pore-forming phase, the subsequent sol-gel reaction results in the formation of solidified gel in which the phase separated domains one rich in solvent the other rich in silica (gel skeleton, matrix) exist. After the solidification of the solution, the gel is aged by setting free the matrix dissolving agent from the precursor. The matrix dissolving agent leads to dissolution and re-precipitation of the inner wall, resulting in the loss of smaller pores and an increase of larger pores thereby creating sharply distributed mesopores.

Prior further solidification the gel skeleton is disintegrated into particles. Such disintegrating step can be performed by stirring as, for example, with an agitator, a high shear mixer (e.g. Ultraturrax®) or by ultrasonics. The particle sizes and distribution can be controlled over a broad range by adjusting the starting time of the disintegration and/or the agitation speed. Surprisingly it has been found that very uniform particle distributions can be obtained by controlling such parameters. Therefore, the process of the invention further offers a simple method to produce particles having a uniform size distribution so that successive classification steps as described in the prior art can be avoided.

Preferably, the gel skeleton is transferred and homogenized to a particulate material by using an agitator. Particle size and distribution can be controlled by selecting the conditions of the process, especially the time period from phase separation until stirring as well as by the speed and size of the agitator. In principle particle formation having a small size and a narrow particle size distribution is promoted by short time periods from phase separation until stirring and by using an agitator having larger blades whereas increased particle sizes is promoted by increasing the time period from phase separation until stirring and using an agitator having a smaller blade.

Typical time periods from phase separation until stirring are in the range from 15 to 120 minutes. For example, if the time period from phase separation until stirring is 15 minutes, and an agitator with a large blade is used a material having a mean particle size of about 11 μm and a narrow particle size distribution ($d_{10}$: 5 μm, $d_{50}$: 11 μm, $d_{90}$: 21 μm) is obtained, if the time period is about 120 minutes a mean particle size of about 200 μm and a broader particle size distribution ($d_{10}$: 5 μm, $d_{50}$: 216 μm, $d_{90}$: 956 μm) is obtained.

In the process of the present invention a water-soluble polymer suitable to induce pore formation by a phase separation process or other pore forming agents are being used to control porosity of the material. The pore forming agents have considerable solubility in water and water-alcohol mixed solvents and have to be uniformly dissolved in the solvent mixture generated during the hydrolysis reaction of metalorganic compound containing hydrolyzable ligands. Pore forming agents which can be used as part of the pore forming phase in producing the porous material according to the invention are desired to have considerable solubility in water and water-alcohol mixed solvents. They have to be uniformly dissolved in the solvent mixture generated during the hydrolysis reaction of the metalorganic compound containing hydrolyzable ligands, such as, for example, silicon alkoxide.

Water-soluble polymers suitable to induce pore formation are, for example, polymeric salts such as poly(sodium styrenesulfonate) or poly(potassium styrenesulfonate), polymeric acids which may dissociate to become polyanion such as poly(acrylic acid), polymeric bases which may dissociate to become polycation such as poly(allylamine) or poly(ethyleneimine), non-ionic polymers having ether oxygen in the main chain such as poly(ethylene oxide), non-ionic polymers having lactone units in the side chain such as poly(vinylpyrrolidone) are suitable examples. Preferred polymers are non-ionic surfactants such as ether derivatives of polyoxyethylene, especially those containing an alkyl-, aryl-, alkylaryl- (e.g. an alkylphenyl), or arylalkyl (e.g. phenylalkyl) residue. Non-ionic surfactants possessing polyoxypropylene residues as hydrophilic moiety, such as polyoxypropylene alkyl ethers can also be used. Preferred polyethylene oxide containing surfactants are those which are derivatized with a lipophilic alkyl group with 8 to 20 C atoms, or with a lipophilic aryl group which can be substituted with one or several alkyl groups, and which have 6 to 25 C-atoms in total. Examples of the latter group of polyethylene oxide containing surfactants are polyoxyethylene nonylphenyl ether, polyoxyethylene octylphenyl ether, or polyoxyethylene (1,1,3,3-tetramethylbutyl)-phenyl ether. However, these examples are not limitative.

The hydrophilic lipophilic balance (HLB) system can be used to facilitate to estimate the behavior of nonionic surfactants, and can be used as guideline for exchanging different non-ionic surfactants. The amount of non-ionic surfactant to be added varies, depending on the type of said non-ionic surfactant and also on the type and the amount of the metal alkoxide added, but may be from 1.0 to 10.0 g, preferably from 1.5 to 6.0 g, per 10 g of the metal alkoxide.

The non-ionic surfactant has the function of inducing both sol-gel conversion and phase separation at the same time. While being gelled, the reaction system is separated into a solvent-rich phase and a silica rich phase. According to a preferred embodiment of the invention is directed to the process as described, wherein the pore forming agent is the non-ionic surfactant.

Metalorganic compound can be applied by hydrolyzing metal alkoxides, metal chlorides, metal salts or coordinated compounds. In this process an organic polymer is used, which is compatible with the solution of the metal alkoxide or its polymer, and which undergoes phase separation during the hydrolysis-polymerization step. This method comprises preparing a gel which has a solvent-rich phase capable of giving macropores of not smaller than about 100 nanometers in size, through sol-gel conversion in the presence of a pore forming agent, and finally drying and calcining the material. The porous inorganic materials produced by this process display connected open macropores. Examples of pore forming agents disclosed in these documents are: Adding lower alkyl alcohols like methanol or ethanol to the gelling mixture can also be used to modify the size of the macropores. In the present invention the sol-gel method is used to control the pore size of the porous inorganic material.

Metalorganic compounds having a hydrolysable ligand like metal alkoxides are used as starting materials with additions of appropriate chemical substances to result in the formation of characteristic phase-separated structure of which solvent-rich pore forming phase converts to the macropore of the dried gel material: Such starting materials and the conditions necessary to hydrolyse these starting materials are known in the art. Preferred metal alkoxides are silicon alkoxides, which may include, for example, tetramethoxysilane (TMOS), tetraethoxysilane (TEOS), methyltrimethoxysilane, ethyltrimethoxysilane and vinyl trimethoxysilane. However, these examples are not limitative. Other suitable metal alkoxides or other suitable metal compounds including mixtures of these compounds are known in the art.

The conditions are chosen so as to hydrolyze the metal compound having a hydrolyzable functional group and to cause polymerization of the metal compound. At the same time the sol-gel transition of the reacting solution and the phase separation into solvent rich phase and a phase rich in metal compound (skeleton phase) are induced. For silicon alkoxides as metal compound having a hydrolyzable functional group the hydrolysis is done in an acidic medium. Diluted organic or inorganic acids are preferred in this case. Especially preferred is the use of acetic acid, hydrochloric acid or nitric acid using concentrations between 1 mmol/l and 2 mol/l. Other acidic media suitable to carry out the hydrolysis of silicon alkoxides are known in the art. Suitable reagents for the hydrolysis of other metalorganic compounds are known in the art as well.

The process of the present invention further includes a precursor, i.e. a precursor for a matrix dissolving agent, which is used to control mesoporosity of the material. Use of a precursor allows its addition from the beginning so that the precursor is and remains dissolved during sol-gel transformation. The liberation of the matrix dissolving agent can be induced later on, for example by heating, which leads to liberation of the matrix dissolving agent by chemical decomposition (thermolysis). Matrix dissolving agents to be liberated from the precursor are basic substances such as ammonia. Precursors which can used in the present invention to liberate ammonia are, for example, urea and organic amides such as formamide, N-methylformamide, N,N,-dimethylformamide, acetamide, N-methylacetamide, and N,N-dimethylacetamide. Preferred precursors are compounds having an amido group or an alkyl amido group, especially preferred is urea. Accordingly, one embodiment of the invention is directed to the process for producing the inorganic particulate material, wherein said precursor of the matrix dissolving agent is a compound having an amido group or an alkylamido group, preferably urea.

The amount of the thermolyzable compound in the reaction system of the present invention may vary, depending on the type of said compound. Urea, for example, may be used in an amount from 0.1 to 3 g, preferably from 0.2 to 2 g, per 10 g of the reaction system (reaction system=sum of all ingredients). The heating temperature for the thermolysis of urea may fall between 60° C. and 200° C. It is preferred that the thermolyzing step is executed in a closed container in order to make the vapor pressure of the thermolyzed product saturated and to rapidly make the solvent have a steady pH-value. After the thermolysis, the pH of the solvent is preferably from 8.0 to 11.0. The time after which the pore structure of the gel stays substantially unchanged under the processing conditions depends on the type of the precursor for the matrix dissolving agent and on the conditions applied (e.g. the temperature); when urea is used as the precursor for the matrix dissolving agent the necessary time typically is between 30 minutes (e.g. at 200° C.) and 30 days (e.g. at 60°

C.). Preferably the gel is treated with urea at 110° C. for about 4 hours which leads to a mesoporous material with ca. 10-13 nm pore size.

After the aging step of the gel by its interaction with the matrix dissolving agent which has been set free from the precursor and prior to removing of solvent from the solidified gel the partly solidified gel skeleton is disintegrated into particles by appropriate means, preferably by stirring with an agitator.

Therefore, a further preferred embodiment of the invention is directed to the process for producing the inorganic particulate material, wherein step (e) is executed by stirring with an agitator, a high shear mixer or by ultrasonics. Early after the phase separation the gel is still soft which would possibly allow the use of an ultra sonic treatment for the particle formation.

The final preparation steps for the manufacture of the porous inorganic particulate materials according to the present invention include an optional rinsing step, e.g. with water, a drying step, and a calcining step. Typically drying is achieved at temperatures between 20 and 80° C.; this step can be facilitated using an oven with air circulation or by applying reduced pressure.

Calcining is typically done at final temperatures between 400 and 900° C. for one to several hours. The final temperature is reached using a temperature program, typically rising the temperature between 50 and 200° C. per hour.

The pore size of macropores is determined using mercury porosimetry. It is also possible to estimate the pore dimensions from scanning electron micrographs (SEM). The pore size of mesopores and their specific surface area are determined using nitrogen adsorption/desorption measurements (BET-method) which are performed by following standard protocols.

The silica particles having mesopores as well as macropores as described in the prior art are prepared by using an emulsion technique (Z. G. Shi et al. (2008), see above), whereas the particles obtained by the process of the present invention are formed by the disintegration of a gel after phase separation. Emulsification leads to spherical droplets of the gel, which are isolated and dried, which results in a particular material having a spherical shape. The process of the present invention does not use emulsification for particle formation but disintegration, and, therefore, leads to a new particulate product, which differs from the prior art product at least in that it has a different particle shape. Accordingly, the invention is also directed to a new inorganic particulate material mainly composed of silicon oxide, wherein the particulate material comprises macropores and mesopores, wherein the macropores have a mean diameter≥0.1 μm and the mesopores have a mean diameter between 2 and 100 nm, obtainable by the process of the present invention as described herein.

The particulate material obtainable by the process has a mean diameter from about 1 μm to about 2000 μm, preferably from about 1 μm to 1000 μm and more preferably from about 1 μm to 500 μm.

Further, one preferred embodiment of the invention is directed to such mesoporous particulate material, wherein said material has an irregular non-spherical shape.

Advantageously the material provided by the present invention can be used as matrix forming agent in a modified release delivery system for a bioactive agent. Therefore, the present invention is also directed to a modified release delivery system comprising a bioactive agent and inorganic mesoporous and macroporous particulate material as it is obtainable according to the process of the present invention.

A bioactive agent, which can be present in the modified release system can be any chemical substance or protein, which are capable of providing a local or systemic biological, physiological, or therapeutic effect in the subject to which it is applied. Preferred examples of a bioactive agent are pharmaceutical drugs, vitamins or minerals. In terms of its activity the bioactive agent, which can be present in the modified release system, can be, for example an agent that act to control or prevent infection or inflammation, enhance cell growth and tissue regeneration, control tumor growth, act as an analgesic, promote anti-cell attachment or enhance bone growth, among other functions. Other suitable bioactive agents can include anti-viral agents, hormones, antibodies, or therapeutic proteins. Still other bioactive agents include prodrugs, which are agents that are not biologically active when administered but upon administration to a subject are converted to bioactive agents through metabolism or some other mechanism. According to a preferred embodiment of the invention the modified release delivery system contain a pharmaceutical drug. Therefore, one embodiment of the invention is directed to a modified release delivery system, wherein the bioactive agent is a pharmaceutical drug.

As used herein, the term "modified release" means that the release of the bioactive agent from the delivery system or a portion thereof upon contact of the dosage form or portion thereof with a liquid medium is different to the release of the same bioactive agent from a conventional immediate release formulation, wherein the release is mainly controlled by the solubility of the bioactive agent in the liquid medium. Accordingly, modified release includes, but is not limited to accelerated release (i.e. an increased dissolution rate), sustained-release, extended release, slow release, delayed release and the like.

The inorganic particulate material comprising macropores and mesopores as it is obtainable by the process of the present invention is especially usable to increase the dissolution of bioactive agents especially suitable to increase the dissolution rate of poorly water-soluble or water-insoluble bioactive agents. Poorly water-soluble substances are understood to have a solubility in water of <10 mg/ml, in particular <5 mg/ml and more particularly <1 mg/ml, practically water-insoluble or insoluble substances are those having a solubility in water of <0.1 mg/ml. The term "water-solubility" or "solubility in water" in the present application refers to the respective solubility measured at 25° Celsius.

Accordingly one further object of the present invention is directed to a modified release system comprising a bioactive agent and inorganic mesoporous and macroporous particulate material as it is obtainable by the process according to the present invention, wherein the bioactive agent has a water-solubility of <about 10 mg/ml, preferably from about 0.1 mg/ml to about 5 mg/ml and more preferably from about <1 mg/ml.

The modified release system according to the present invention contains the bioactive agent in an amount of from about 0.1 to about 90% by weight, preferably from about 0.2 to about 75% by weight, more preferably from about 5 to about 40% by weight most preferably from about 10 to about 30% by weight. Thus the invention is also directed to a modified release system as described herein, wherein the bioactive agent is present in an amount of from about 0.1 to about 90% by weight, preferably from about 0.2 to about 75% by weight, more preferably from about 5 to about 40% by weight most preferably from about 10 to about 30% by weight.

The bioactive agent can be applied to the inorganic particulate material by using the loading techniques known in the art, as, for example, by adsorption from a solution of the bioactive agent in a suitable solvent to the inorganic material and subsequent separation, by wetness impregnation of the inorganic material with a concentrated solution of the bioactive agent in a suitable solvent such as, for example, ethanol, $CH_2Cl_2$ or acetone and subsequent solvent evaporation, by spray-drying of a mixture of bioactive agent in a suitable solvent, by heating of a mixture of the bioactive agent and the particulate material or by drug loading with supercritical fluids.

The modified release system can be formulated as an oral, a topical or a parenteral administration form, preferably as an oral administration form. Consequently, the invention is further directed to the use of the modified release system as described herein, wherein said system is an oral or a topical or a parenteral administration form.

Suitable for oral administration forms include tablets, capsules, powders, dragées, suspensions; suitable topical administration forms include ointments, creams, suspensions, lotions, powders, solutions, pastes, gels, sprays, aerosols or oils.

If an oral administration form is used, tablets, capsules and powders are preferred, if a topical administration form is used, ointments, creams, suspensions and powders are preferred. Accordingly, the invention is also directed to a modified release system as described herein, wherein said release system is an oral application form, which is a tablet, a capsule, a powder, or a dragée, or a topical administration form, which is an ointment, a cream, a suspension or a powder and a parenteral administration form, which comprises microparticles or is an implant.

The modified release system is suitable to be used for the administration of at least one bioactive agent to mammal, preferably to a human. Accordingly, the invention is also directed to the use of the modified release system as described herein for the administration of at least one bioactive agent to a mammal, preferably to a human.

The application forms described above are well known in the art. For example, if the modified release system is in the form of a tablet or capsule, the bioactive agent loaded inorganic material can be combined with an oral, non-toxic and pharmaceutically acceptable inert excipient, such as, for example, ethanol, glycerol, water and the like. Powders can be composed of the bioactive agent loaded inorganic material itself, which may be further comminuted, or can be prepared, for example, by mixing the bioactive agent loaded inorganic, which may have been comminuted, with a comminuted pharmaceutical excipient, such as, for example, an edible carbohydrate, such as, for example, starch or mannitol. A flavour, preservative, dispersant and dye may likewise be present.

Capsules can be produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the active agent loaded in a inorganic, which may have been comminuted in a suitable manner, with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The bioactive agent loaded inorganic material can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

For the treatment of external tissue, for example mouth and skin, the formulations are preferably applied as topical ointment or cream. In the case of formulation to give an ointment, the bioactive agent loaded inorganic material can be employed either with a paraffinic or a water-miscible cream base. Alternatively, the bioactive agent loaded inorganic material can be formulated to give a cream with an oil-in-water cream base or a water-in-oil base.

The term "implant" denotes a solid modified release delivery system, which is deposited in any suitable body tissues or cavities to form a reservoir or pool which slowly migrates to surrounding tissues and organs and eventually becomes systemically distributed. However, these distinctions are not always rigidly adhered to in the art, and consequently, it is contemplated that there is included within the scope of the present invention liquid implants and solid depots, and even mixed solid and liquid forms for each.

Also included are implants which are placed beneath the epidermal layer of the skin, i.e. between the epidermis and the dermis of the skin of the patient being treated. Such an implant will be formulated in accordance with well known principles and materials commonly used in this delivery technology, and may be prepared in such a way as to provide controlled-, sustained-, and/or delayed-release of the active ingredient into the systemic circulation of the patient. Advantageously such type of implant can be easily administered and removed by minimal incision or can be applied by using an implant syringe, which are well known in the art for such purpose.

The solid modified release delivery system can be also parenterally applied in the form of microparticles via a syringe using a carrier liquid. Preferably, the microparticles are mixed with the carrier liquid to be injected into a patient. In one embodiment the microparticles mixed with an organic solvent to produce a liquid or gel which may be injected into a patient.

Further formulations adapted for topical application in the mouth encompass lozenges, pastilles and mouthwashes.

The examples explain the invention without being restricted thereto.

EXAMPLE 1

In a three necked flask (equipped with an overhead stirrer with a small blade, 7.6 cm diameter) 30.45 g PEO and 27.00 g urea are dissolved in 300 mL of 0.01 M acetic acid and mixed at room temperature for 10 min. The solution is then cooled down to 5.0° C. followed by the addition of 150 mL TMOS without stirring. The resulting mixture is then stirred for 30 min at 5.0° C. and subsequently heated up to 30° C. for another 20 minutes. The stirring is then stopped and a phase separation takes place (solution changes from transparent to a white colour). 15 min after the phase separation the semi solid silica gel is stirred with a speed of 450 rpm for 3.5 h and with 300 rpm over night. Afterwards the silica gel is poured into a pressure resistant glass bottle and aged in a steam autoclave for 4 h at 110° C. The solvent is exchanged over a glass suction filter in four steps: purified water, nitric-acid, purified water and water/ethanol (2:1). The silica is washed four times with about 200 mL of each solvent and filtered to dryness. The semi-dried silica gel is replaced into an evaporating dish which is covered by a paper filter followed by a drying step in an oven for 5 days at 40° C.

The dried gel is calcined for 4 h at 600° C. with a heating rate of 50 K/h. The calcined gel is analysed by Hg-Intrusion and $N_2$-Adsorption/Desorption (BET-measurement). Further, the particle size distribution is measured by the Malvern Laserbeugung method.

Particle measurement of this and all other Examples was performed using the following Instruments:

Hg-Intrusion: PoreMaster 60 from Quantachrome Instruments, 1900 Corporate Drive Boynton Beach, Fla. 33426 USA;

BET: Accelerated Surface Area and Porosimetry System ASAP® 2420 from Micromeritics Instrument Corporation, 4356 Communications Drive, Norcross, Ga. 30093-2901, USA;

Malvern Mastersizer 2000 from Malvern Instruments Ltd, Enigma Business Park, Grovewood Road, Malvern, Worcestershire WR14 1XZ, United Kingdom.

Macropore size: 4.81 µm
Mesopore size: 10.1 nm
Surface area: 322 m²/g
Particle size distribution: $d_{10}$=6 µm, $d_{50}$=22 µm, $d_{90}$=92 µm

EXAMPLE 2

In a three necked flask (equipped with an overhead stirrer with a large blade, 8.8 cm) 30.45 g PEO and 27.00 g urea are dissolved in 300 mL of 0.01 M acetic acid and mixed at room temperature for 10 min. The solution is then cooled down to 5.0° C. followed by the addition of 150 mL TMOS without stirring. The resulting mixture is then stirred for 30 min at 5.0° C. and subsequently heated up to 30° C. for another 20 minutes. The stirring is then stopped and a phase separation takes place (solution changes from transparent to a white colour). 15 min after the phase separation the semi solid silica gel is stirred with a speed of 450 rpm for 3.5 h and with 300 rpm over night. Afterwards the silica gel is poured into a pressure resistant glass bottle and aged in a steam autoclave for 4 h at 110° C. The solvent is exchanged over a glass suction filter in four steps: purified water, nitric-acid, purified water and water/ethanol (2:1). The silica is washed four times with about 200 mL of each solvent and filtered to dryness. The semi-dried silica gel is replaced into an evaporating dish which is covered by a paper filter followed by a drying step in an oven for 5 days at 40° C.

The dried gel is calcined for 4 h at 600° C. with a heating rate of 50 K/h. The calcined gel is analysed by Hg-Intrusion and $N_2$-Adsorption/Desorption (BET-measurements). Further, the particle size distribution is measured by the Malvern Laserbeugung method.

Macropore size: 3.99 µm
Mesopore size: 10.2 nm
Surface area: 321 m²/g
Particle size distribution: $d_{10}$=5 µm, $d_{50}$=11 µm, $d_{90}$=21 µm

EXAMPLE 3

In a three necked flask (equipped with an overhead stirrer with a large blade, 8.8 cm) 30.45 g PEO and 27.00 g urea are dissolved in 300 mL of 0.01 M acetic acid and mixed at room temperature for 10 min. The solution is then cooled down to 5.0° C. followed by the addition of 150 mL TMOS without stirring. The resulting mixture is then stirred for 30 min at 5.0° C. and subsequently heated up to 30° C. for another 20 minutes. The stirring is then stopped and a phase separation takes place (solution changes from transparent to a white colour). 30 min after the phase separation the semi solid silica gel is stirred with a speed of 450 rpm for 3.5 h and with 300 rpm over night. Afterwards the silica gel is poured into a pressure resistant glass bottle and aged in a steam autoclave for 4 h at 110° C. The solvent is exchanged over a glass suction filter in four steps: purified water, nitric-acid, purified water and water/ethanol (2:1). The silica is washed four times with about 200 mL of each solvent and filtered to dryness. The semi-dried silica gel is replaced into an evaporating dish which is covered by a paper filter followed by a drying step in an oven for 5 days at 40° C.

The dried gel is calcined for 4 h at 600° C. with a heating rate of 50 K/h. The calcined gel is analysed by Hg-Intrusion and $N_2$-Adsorption/Desorption (BET-measurements). Further, the particle size distribution is measured by the Malvern Laserbeugung method.

Macropore size: 1.7 µm
Mesopore size: 10.1 nm
Surface area: 321 m²/g
Particle size distribution: $d_{10}$=5 µm, $d_{50}$=166 µm, $d_{90}$=501 µm

EXAMPLE 4

In a three necked flask (equipped with an overhead stirrer with a small blade, 7.6 cm) 30.45 g PEO and 27.00 g urea are dissolved in 300 mL of 0.01 M acetic acid and mixed at room temperature for 10 min. The solution is then cooled down to 5.0° C. followed by the addition of 150 mL TMOS without stirring. The resulting mixture is then stirred for 30 min at 5.0° C. and subsequently heated up to 30° C. for another 20 minutes. The stirring is then stopped and a phase separation takes place (solution changes from transparent to a white colour). 2 hours after the phase separation the semi solid silica gel is roughly cracked with a spatula and afterwards stirred with a speed of 450 rpm for 3.5 h and with 300 rpm over night. Afterwards the silica gel is poured into a pressure resistant glass bottle and aged in a steam autoclave for 4 h at 110° C. The solvent is exchanged over a glass suction filter in four steps: purified water, nitric-acid, purified water and water/ethanol (2:1). The silica is washed four times with about 200 mL of each solvent and filtered to dryness. The semi-dried silica gel is replaced into an evaporating dish which is covered by a paper filter followed by a drying step in an oven for 5 days at 40° C.

The dried gel is calcined for 4 h at 600° C. with a heating rate of 50 K/h. The calcined gel is analysed by Hg-Intrusion and $N_2$-Adsorption/Desorption (BET-measurements). Further, the particle size distribution is measured by the Malvern Laserbeugung method.

Macropore size: 1.7 µm
Mesopore size: 10.1 nm
Surface area: 321 m$^2$/g
Particle size distribution: $d_{10}$=5 µm, $d_{50}$=166 µm, $d_{90}$=501 µm

EXAMPLE 5

In a three necked flask (equipped with an overhead stirrer with a large blade, 8.8 cm) 30.45 g PEO and 27.00 g urea are dissolved in 300 mL of 0.01 M acetic acid and mixed at room temperature for 10 min. The solution is then cooled down to 5.0° C. followed by the addition of 150 mL TMOS without stirring. The resulting mixture is then stirred for 30 min at 5.0° C. and subsequently heated up to 30° C. for another 20 minutes. The stirring is then stopped and a phase separation takes place (solution changes from transparent to a white colour). 30 min after the phase separation the semi solid silica gel is stirred with a speed of 450 rpm for 3.5 h and with 300 rpm over night. Afterwards the silica gel is poured into a pressure resistant glass bottle and aged in a steam autoclave for 4 h at 110° C. The solvent is exchanged over a glass suction filter in four steps: purified water, nitric-acid, purified water and water/ethanol (2:1). The silica is washed four times with about 200 mL of each solvent and filtered to dryness. The semi-dried silica gel is replaced into an evaporating dish which is covered by a paper filter followed by a drying step in an oven for 5 days at 40° C.

The dried gel is calcined for 4 h at 600° C. with a heating rate of 50 K/h. The calcined gel is analysed by Hg-Intrusion and $N_2$-Adsorption/Desorption (BET-measurements). Further, the particle size distribution is measured by the Malvern Laserbeugung method.

For the purpose of a subsequent rehydroxylation of the silica surface (transformation of siloxane groups to hydrophilic silanol groups) the calcined silica gel is suspended in a beaker with water which is placed in an autoclave for 3 h at 130° C. Afterwards the rehydroxylated gel is washed with methanol over a glass suction filter until all solvent is removed. The silica gel is then placed in an evaporating dish covered with a paper filter and dried in an oven for 5 days at 40° C.

The resulting material possess hydrophilic properties due to a maximization of silanol groups.

Macropore size: 1.43 µm
Mesopore size: 11.1 nm
Surface area: 328 m$^2$/g
Particle size distribution: $d_{10}$=3 µm, $d_{50}$=25 µm, $d_{90}$=562 µm
Example for Drug Loading Itraconazole, a synthetic triazole antifungal agent, which is poorly soluble in aqueous solutions (1 ng/mL at pH 7 and 4 µg/mL at pH 1; see Six, K. et al., *Eur J Pharm Sci* 24 (2005) 179-186), was used as model drug.

The silica material of the present invention was drug loaded with itraconazole by using wetness impregnation. For this purpose 1.0 g of itraconazole was dissolved in 130 mL of acetone at 53° C. A 250 mL three necked flask (heated by a water bath at 60° C.; equipped with an overhead stirrer and paddle) was filled with 2.3 g of silica material synthesized in accordance to Example 5. The itraconazole solution was added pro rata (10 mL per impregnation step) to the flask while acetone was evaporated by a nitrogen stream under stirring. The procedure of impregnating and subsequently evaporating was repeated until the entire itraconazole solution was evaporated. Additionally, the obtained powder was dried under vacuum at 40° C. over night. The resulting drug load aimed to 30% by weight.

The dissolution rates of itraconazole loaded formulation prepared as set forth above and pure crystalline itraconazole was tested using USP Apparatus II (rotating paddle) dissolution tester with on-line UV sampler and measurement system (conditions: simulated gastric fluid (SGF) without pepsin; 1000 mL vessel; 37° C.; 75 rpm; 0.1% sodium dodecyl sulphate (SDS)).

The itraconazole loaded samples tested contained 50 mg of itraconazole which was confirmed by high performance liquid chromatography (HPLC) with UV detector, pure crystalline itraconazole was tested in the same amount (50 mg).

BRIEF DESCRIPTION OF THE DRAWING

FIG. 1 summarizes the dissolution rates of the samples tested.

The invention claimed is:
1. Inorganic particulate material composed of silicon oxide, wherein the particulate material comprises macropores and mesopores wherein the macropores have a mean diameter >0.1 µm and the mesopores have a mean diameter between 2 and 100 nm, which is obtained by a process for producing inorganic particulate material mainly composed of silicon oxide, wherein the particulate material comprises mesopores and macropores and the process includes the steps of:
(a) dissolving a water-soluble polymer or another pore forming agent and a precursor for a matrix dissolving agent in a medium that promotes the hydrolysis of a metalorganic compound;
(b) mixing a metalorganic compound or a mixture of metalorganic compounds which contains hydrolyzable ligands to promote a hydrolysis reaction;
(c) solidifying the mixture through a sol-gel transition, wherein a gel is prepared which has three dimensional interconnected phase domains, one rich in solvent and the other rich in inorganic component, in which surface pores are contained;
(d) disintegrating the gel into particles 15 to 120 minutes after the phase separation of step (c), wherein a uniform particle size distribution is determined by controlling the time from phase separation to disintegration, resulting in particles having a mean diameter from 1 µm to 2000 µm;
(e) setting the matrix dissolving agent free from its precursor, wherein the matrix dissolving agent modifies the structure of said inorganic component; and

(f) removing the solvent by evaporation drying and/or heat-treatment.

2. Inorganic particulate material composed of silicon oxide, wherein the particulate material comprises macropores and mesopores wherein the macropores have a mean diameter >0.1 µm and the mesopores have a mean diameter between 2 and 100 nm, which is obtained by a process for producing inorganic particulate material mainly composed of silicon oxide, wherein the particulate material comprises mesopores and macropores and the process includes the steps of:

(a) dissolving a water-soluble polymer or another pore forming agent and a precursor for a matrix dissolving agent in a medium that promotes the hydrolysis of a metalorganic compound;

(b) mixing a metalorganic compound or a mixture of metalorganic compounds which contains hydrolyzable ligands to promote a hydrolysis reaction;

(c) solidifying the mixture through a sol-gel transition, wherein a gel is prepared which has three dimensional interconnected phase domains, one rich in solvent and the other rich in inorganic component, in which surface pores are contained;

(d) disintegrating the gel into particles 15 to 120 minutes after the phase separation of step (c), wherein the mean diameter of the particles is from 1 µm to about 2000 µm;

(e) setting the matrix dissolving agent free from its precursor, wherein the matrix dissolving agent modifies the structure of said inorganic component; and (f) removing the solvent by evaporation drying and/or heat-treatment.

3. The inorganic mesoporous particulate material according to claim 1, wherein said material has an irregular non-spherical shape.

4. A modified release delivery system comprising a bioactive agent and inorganic mesoporous particulate material according to claim 1.

5. A modified release delivery system according to claim 4, wherein the bioactive agent is a pharmaceutical drug.

6. A modified release delivery system according to claim 4, wherein the bioactive agent has a water-solubility of <about 10 mg/ml.

7. A modified release delivery system according to claim 4, wherein the bioactive agent is present in an amount of from about 0.1 to about 90% by weight.

8. A modified release delivery system according to claim 4, wherein said system is an oral or a topical or a parenteral administration form.

9. A modified release delivery system according to claim 8, wherein the oral administration form is a tablet or capsule, a powder, or a dragée, the topical administration form is an ointment, a cream, a powder or a suspension and the parenteral administration form is a microparticle or an implant.

10. A method for the administration of at least one bioactive agent to a mammal, comprising administering the bioactive agent as part of a modified release system of claim 4.

11. Method according to claim 10, wherein said administration to the mammal is an oral or a topical or a parenteral administration.

12. The inorganic mesoporous particulate material according to claim 1, wherein the process further includes the step (g) calcining the particles.

13. The inorganic mesoporous particulate material according to claim 1, wherein the macropores have a mean diameter >0.1 µm and the mesopores have a mean diameter between 2 and 100 nm.

14. The inorganic mesoporous particulate material according to claim 1, wherein in the process said precursor of the matrix dissolving agent is a compound having an amido group or an alkylamido group.

15. The inorganic mesoporous particulate material according to claim 1, wherein in the process step (d) is executed by stirring with an agitator.

16. The inorganic mesoporous particulate material according to claim 1, wherein in the process the pore forming agent is a non-ionic surfactant.

17. The inorganic mesoporous particulate material according to claim 1, wherein in the process said precursor of the matrix dissolving agent is a compound having a urea group.

18. The inorganic mesoporous particulate material according to claim 1, wherein in the process the mean diameter of the particles is from about 1 µm to about 500 µm.

19. The inorganic mesoporous particulate material according to claim 1, wherein in the process the particles made have an irregular non-spherical shape.

20. The inorganic mesoporous particulate material according to claim 1, wherein in the process step (d) is the disintegrating of the gel into particles 15 to 30 minutes after the phase separation of step (c).

* * * * *